United States Patent [19]

Hancock

[11] Patent Number: 4,651,263
[45] Date of Patent: Mar. 17, 1987

[54] SUPPORT OF SUN TANNING CANOPIES

[76] Inventor: Michael R. Hancock, Flat 2, Chandler House, North Quay, Douglas, Isle of Man

[21] Appl. No.: 724,094

[22] Filed: Apr. 17, 1985

[30] Foreign Application Priority Data

Apr. 19, 1984 [GB] United Kingdom ............... 8410256

[51] Int. Cl.⁴ .............................................. F21V 21/18
[52] U.S. Cl. .................................. 362/402; 128/371; 250/494.1; 362/401
[58] Field of Search ............... 362/401, 402, 217, 220; 128/371; 250/494.1

[56] References Cited

U.S. PATENT DOCUMENTS

| | | | |
|---|---|---|---|
| 1,823,535 | 9/1931 | Frutkow et al. | 362/402 |
| 2,709,090 | 5/1955 | Zeeb. | |
| 2,757,941 | 8/1956 | Zeeb. | |
| 2,844,391 | 7/1958 | Albers. | |
| 2,941,776 | 6/1980 | Lauterbach | 362/402 |
| 3,958,116 | 5/1976 | Jones | 362/401 |
| 4,095,113 | 6/1978 | Wolff | 250/494.1 |
| 4,277,855 | 7/1981 | Poss | 128/371 |
| 4,437,144 | 3/1984 | Guenther | 362/401 |
| 4,469,102 | 9/1984 | Fish | 128/371 |
| 4,469,951 | 9/1984 | Coco et al. | 250/494.1 |

*Primary Examiner*—E. Rollins Cross
*Attorney, Agent, or Firm*—Kenway & Jenney

[57] ABSTRACT

A sun tanning canopy is carried on an arm extending from a sleeve slidably engaging a vertical support column for heightwise movement up and down the said column, the sleeve and canopy being supported by a counterbalancing device consisting a coiled constant tension spring the upper free end of which is secured to the top of the column and the lower coiled end supported by abutment means secured to the said sleeve, whereby the heightwise position of the sleeve in the column can be varied by the application of slight upward or downward pressure on the sleeve or canopy.

12 Claims, 7 Drawing Figures

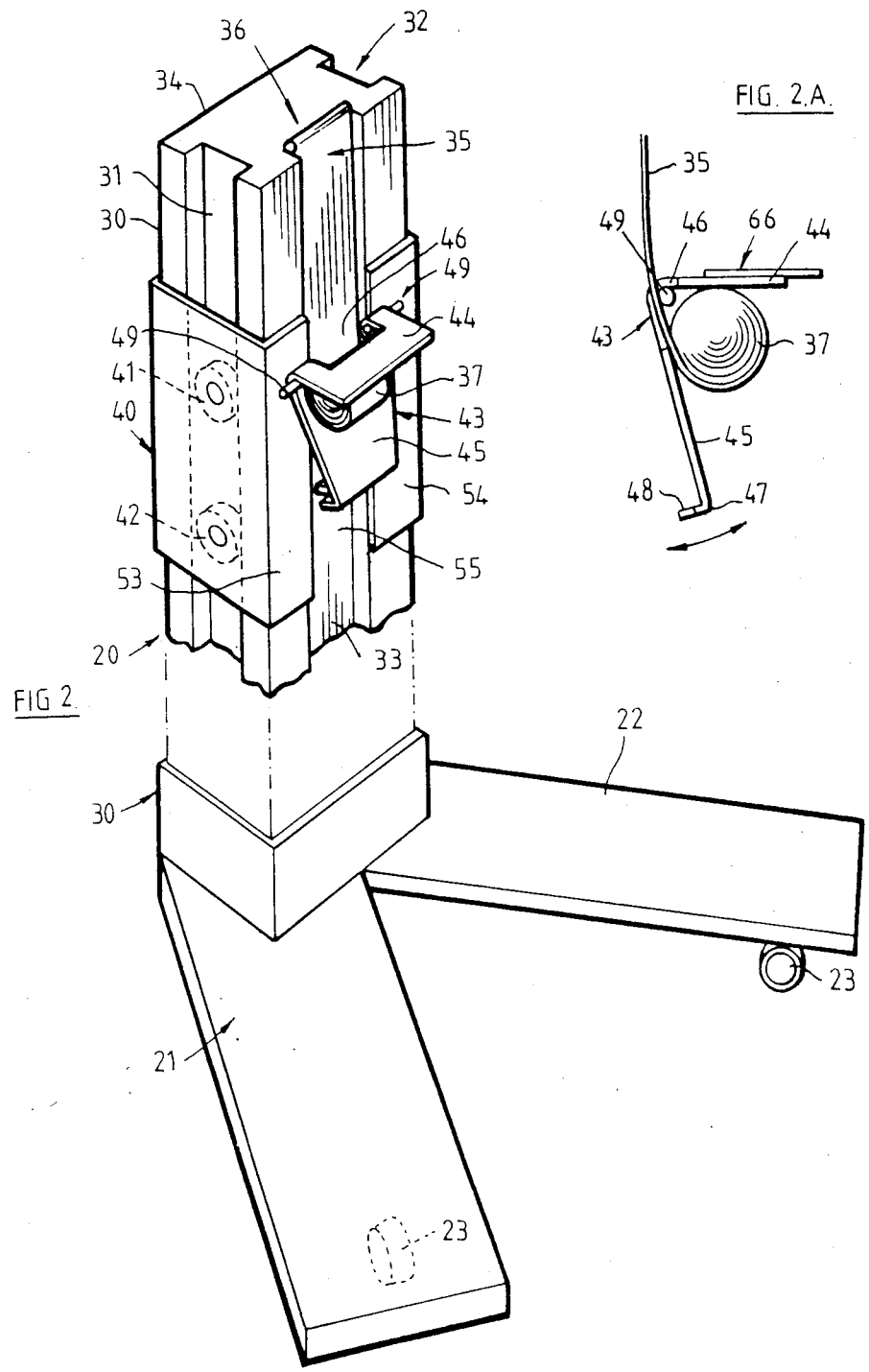

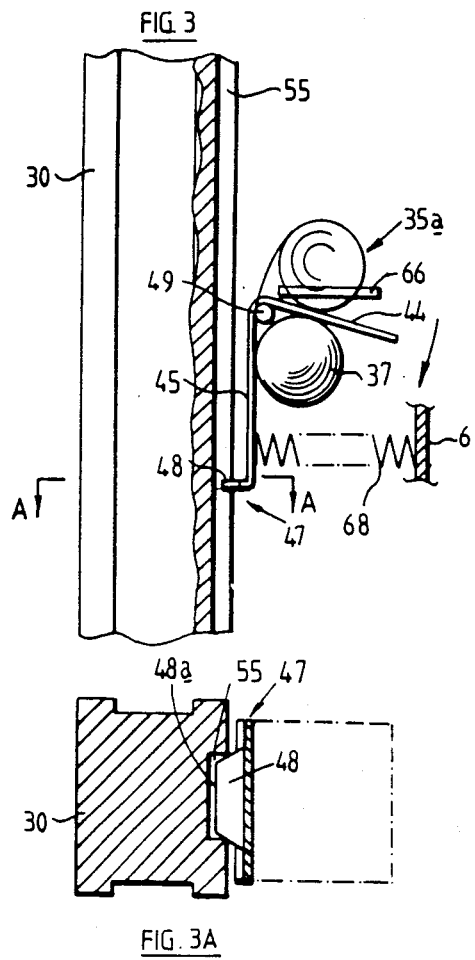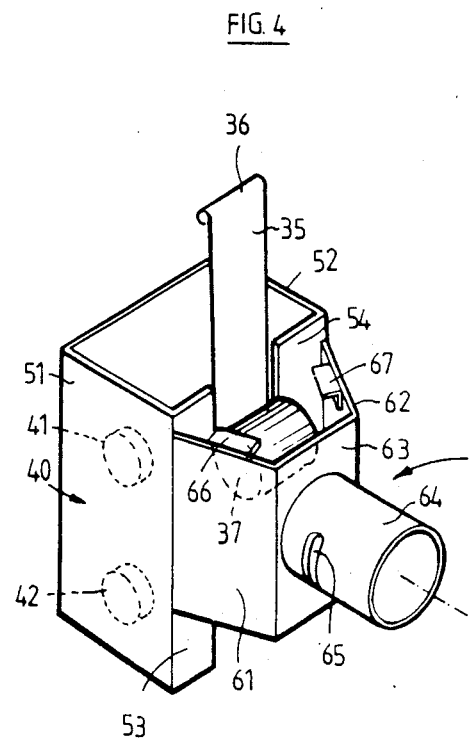

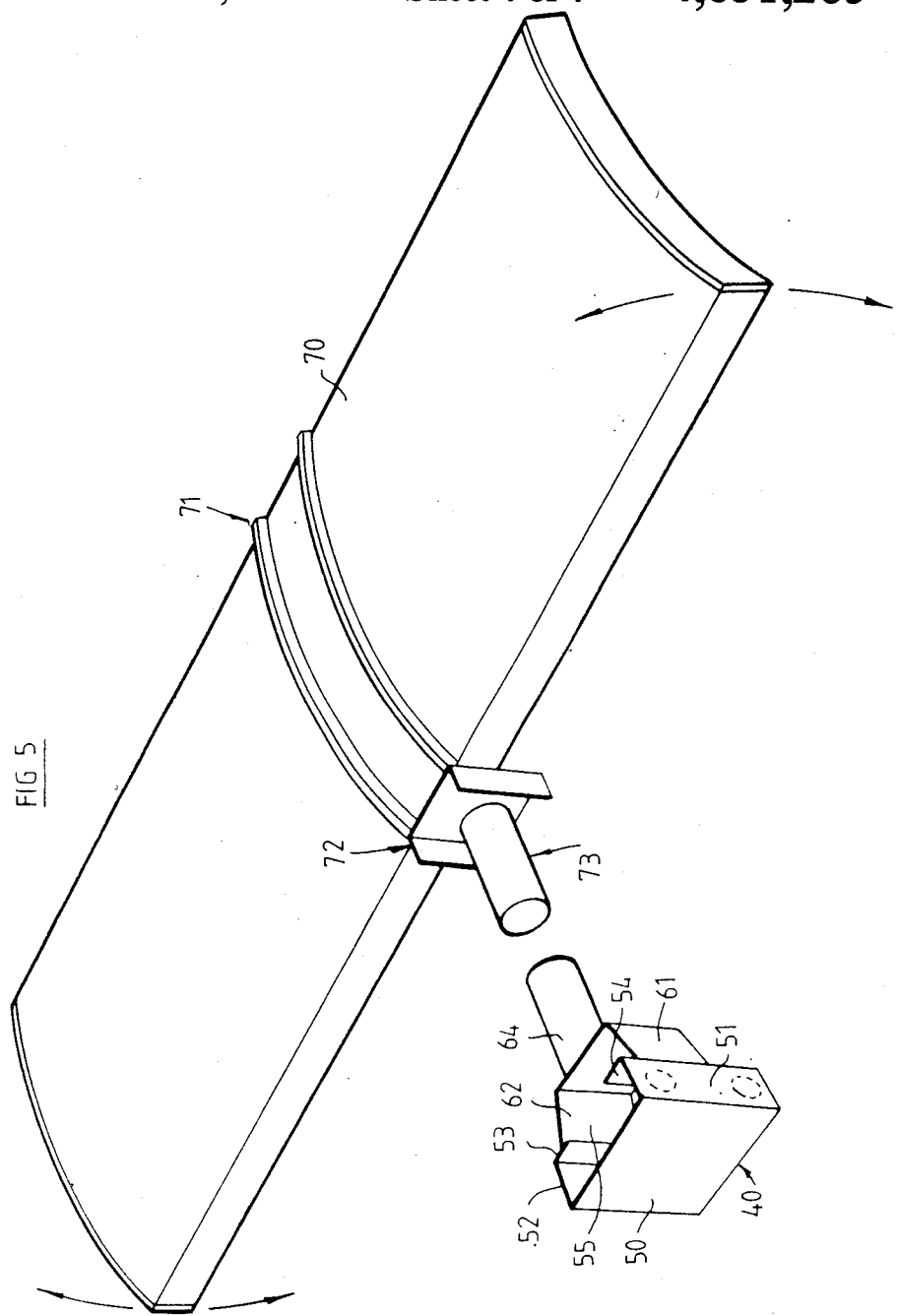

SUPPORT OF SUN TANNING CANOPIES

The present invention is concerned with an improvement in methods of supporting sun tanning canopies.

Various methods of supporting sun tanning canopies have been proposed aimed at producing easy access to and from positions under the canopy, obtaining the optimum height for the canopy above a user and for pivoting the canopy into a vertical position for storage purposes. One such method is disclosed in my copending application No. 8305776.

However the problems of enabling rapid exit from under the canopy and obtaining fully variable vertical positioning of the canopy has not been adequately solved.

I have now discovered a method and apparatus which substantially overcomes the forementioned problems. The method involves mounting the canopy at the end of an arm, optionally pivotal about a horizontal axis, the other end of which is secured to a sleeve that slidably engages the vertical column of a support stand, the weight of the canopy and the sleeve being counterbalanced by means positioned on or within the said column whereby the vertical position of the canopy can be set at any point between a lowermost position and a position adjacent the top of the support column, only minimal pressure on a canopy being required to move it vertically up or down the said column.

In this method of supporting the canopy a vertical position to suit the needs of a specific user is readily obtained. The canopy readily accommodates different heights of beds or benches and in the event that the user wishes to exit rapidly from beneath the canopy it is easily pushed upwards to an out-of-the-way position.

The present method of supporting the canopy is especially suited to use with the lightweight canopy disclosed in my copending U.K. applications No. 8322037 and 8323098.

Counterbalancing may be achieved with weights moveable within the column and attached at one end of a suitable wire or cord passing over a pulley at the top of the column, the other end of the wire or cord being secured to the sleeve carrying canopy. The wire or cord may be replaced by a chain and the pulley by a sprocket.

The weights may consist of or include the fluorescent tube control gear which will normally be located within the column, the control gear then being connected to the control panel, which may be carried on the column or may be remote from the column, by suitable extensible electric cable. Alternatively pairs of compression or extension coil springs may be employed, one such spring acting between the sleeve, or means secured to the sleeve, and the base of the column and another identical spring acting between the sleeve and the top of the support column.

The preferred method of counterbalancing, however, is to use a spring having an approximate constant force over the required extension range such springs are sold under the trade name "Tensator" by Tensator Limited of Newport Pagnel Buckinghamshire, England.

It is preferred that the column supporting the sleeve includes a stop means located near the lower end which will prevent the canopy being moved lower than a predetermined distance above a user lying on a bed or bench. The vertical positioning of such means may be made adjustable to suit individual requirements.

Embodiments of the invention diagrammatically illustrating aspects of the invention will now be described with reference to the accompanying drawings in which:

FIG. 2 is a view from the front of part of a second embodiment;

FIG. 2a is a side view of item 43 of FIG. 2;

FIG. 3 is a side view of a portion of FIG. 2 illustrating item 43 in a second position;

FIG. 3a is a horizontal section through A—A of FIG. 3;

FIG. 4 is a detailed illustration of the sleeve 40 of FIG. 2; and

FIG. 5 is an illustrations of the manner of mounting a sun tanning panel to the sleeve of FIG. 4.

Figure 1:
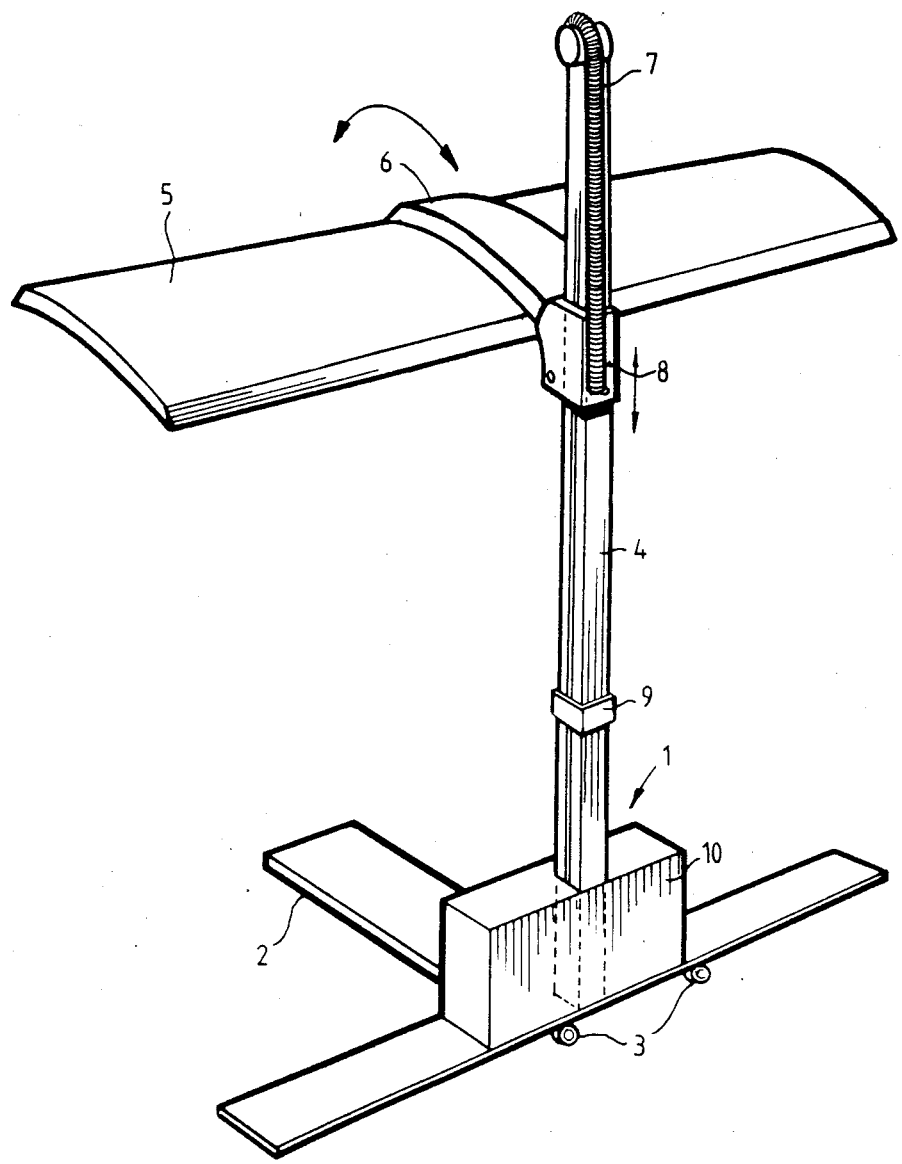
FIG. 1 is a perspective view of a first embodiment of the present invention.

In FIG. 1 of the drawings a support means, generally indicated at 1 includes a T-shaped stand of thin section designed to slip under a divan bed and carried on a pair of castors 3 mounted at the rear of the stand on either side of a vertical support column 4. The vertical support column 4 carries a canopy 5 including a plurality of fluorescent tubes (not shown) supported at one end of an arm 6 extending outwardly of a sleeve 8. Arm 6 is mounted on sleeve 8 for pivotal movement about a substantially horizontal axis to enable the canopy to be tilted between the horizontal position (illustrated) and a vertical position for ease of storage. The sleeve 8 is in sliding engagement with the outer surfaces of the support column 4. Its position on column 4 is controlled by a constant force coil spring 7 positioned at the top of the column, one end of which spring 7 is secured to the sleeve 8 and the other end to a rotatable axle about which the spring coils. Friction between the sleeve and the column prevents free movement of the sleeve in the absence of an external force. Only a minimal force is required to move the sleeve upwardly and downwardly of the column to any desired position from the top to a fixed position near the base of the column. An adjustable stop means 9 is positioned near the base of the column at a height arranged to prevent the canopy being lowered beyond a predetermined distance above a user lying on a bed or bench beneath the canopy.

Canopy 5 is of lightweight construction such as that disclosed in my copending U.K. applications No. 8322037 and 8323098.

Because the spring has a constant tension over a predetermined extension, the vertical position of the canopy can be readily adjusted to suit the needs of a user and, in the event of the user wishing to move rapidly from beneath the canopy it is only necessary that the user reach up to push the canopy to an out-of-the-way position.

The spring 7 may, in its extended condition, lie on the outside of the column, as shown and may be encased within a telescopic plastic sleeve extending around the column (not shown) or it may be located within the column and attached to the sleeve through means extending from the sleeve through a longitudinal slot formed in the column.

The fluorescent tube chokes and other control gear may be conveniently located in the box arrangement 10 at the base of the column with the control panel mounted on the box or contained within a remote unit attached to the stand by suitable cabling.

The force required to move the sleeve vertically up and down the column 4 may be reduced by arranging that the sleeve include rollers located between the inner walls thereof and the column to facilitate relative movement by reducing the frictional drag between the sleeve and the column. A preferred embodiment using a constant tension spring to counterbalance a sun-tan canopy is described with reference to FIGS. 2 to 4 of the drawings.

A canopy support. generally indicated at 20 (the fluorescent tube panel having being omitted for reason of clarity) is shown with particular reference to FIG. 2 and comprises a vertical support column 30 the lower end of which is mounted at the junction of a pair of feet 21 and 22 extending outwardly and subtending an angle of about 90° and which are carried on castors 23 (2 only shown).

Support column 30 is formed from pressed steel and has a rectangular cross section recessed on three sides to provide vertically extending channels 31, 32 and 33. Channels 31 and 32 are formed to receive two pairs of rollers 41 and 42 attached to opposite sides 51 and 52 of sleeve 40; the said rollers engaging the side walls of channels 31 and 32 to enable sleeve 40, and its associated panel, to move easily up and down the column 30.

Channel 33 receives constant tension spring 35. Free end 36 of spring 35 is secured to the top 34 of column 30. The coiled end 37 of spring 35 is located beneath the upper arm 44 of a pressure plate/braking mechanism generally indicated at 43.

Sleeve 40, best seen in FIG. 4, is formed to wrap around column 30 and includes rear and side portions 50. 51 and 52 respectively, that are a sliding fit over the corresponding sides of column 30, and front portions 53, 54 that are also a sliding fit over the front of column 30 and provide between the edges of the two portions, a vertical gap 55 of substantially the same width as channel 33 of column 30. An inner panel support bracket 60 includes outwardly extending arms 61, 62 each secured at one end to portions 53 and 54 respectively of sleeve 40, the other ends being joined by member 63 to provide an open box structure extending outwardly of column 30. An inner pivot tube 64 is secured to and extends horizontally from member 63. Abutment plates 66, 67 are secured to the upper edge portions of arms 61, 62 and extend inwardly towards, but not overlapping channel 33 of column 30.

The pressure plate/braking mechanism 43 is contained within the box structure formed by bracket 60 and consists of a substantially Z-shaped plate having an upper outwardly extending arm portion 44 dimensioned to extend across gap 55 of sleeve 40, downwardly and outwardly extending arm portion 45 and a lower inwardly directed portion 47. Slot 46 is formed in arm 44 and in the upper end of portion 45 through which spring 35, located in the angle formed between arms 44 and 45 passes into channel 33.

Mechanism 43 is mounted on sleeve 40 for pivotal movement about horizontally positioned pivot pins 49. The tension in spring 35 causes the coil portion 37 to urge arm 44 upwardly against the abutment 66 and 67 thereby providing support for the canopy panel 70 that is attached to inner pivot tube 64 as hereinafter described.

The lower arm 47 of mechanism 43 includes an inwardly extending and tapering blade portion 48 best see with reference to FIG. 3a, Edge 48a of blade portion 48 is dimensioned to enter channel 33, the taper in blade 48 being such that when edge 49 enters channel 33 it prevents the said edge 49 from making contact with the rear of the panel, the sides of the taper engaging the outer edges of the side of channel 33.

Panel 70 having the same construction as panel 5 of FIG. 1. is secured beneath an arm portion 71 which, in turn, is secured to outer bracket 72. Outer pivot tube 73 extends at right angles from bracket 72 for slidable, pivotal engagement within inner tube 64. Said tube 73 includes a radially extending retractable stop (not shown) that, when tube 73 is inserted within tube 64, engages an arcuate circumferential slot 65 formed in pivot 64 to define the extent of pivotal movement of panel 70 between the horizontal and vertical positions.

As stated with respect to the embodiment FIG. 1, the vertical height of the panel can be readily adjusted by moving sleeve 40 up or down column 30, light hand pressure, for example on the panel, only being required to effect the necessary movement, the panel being supported through the action of coil 37 of spring 35 acting against arm 44 of mechanism 43 which portion, in turn. acts against abutments 66 and 67 of bracket 60 supporting panel 70.

In the event that spring 35 breaks or becomes detached from the top of column 30, e.g. as shown in FIG. 3 in which a broken end of spring 35 is shown coiled (35a) above arm 44 of mechanism 43, the upwardly directed force applied by spring 35 no longer urges arm 44 against abutments 66 and 67 and the mechanism 43 pivots about pins 49 thereby causing edge 49 of blade 48 to enter channel 33 and to become wedged against the edges of the wall thereof to provide a brake against downward movement of the sleeve and the associated panel. The blade 48 may be positively urged towards channel 33 by means of a compression spring 68 acting between the inner face of member 63 and the downwardly directed portion 45 of mechanism 43.

When not required panel 70 may be pivoted about the. horizontal axis of tubes 73 and 64 into the vertical position for storage. Column 30 may. if required, be pivotally mounted on feet 21,22 for movement through an arc of about 22½° through a line bisecting 21,22 in order to allow the panel to be moved into a position where, in the vertical position, it overlies one of the legs 21,22 for storage purposes.

I claim:

1. A method of mounting a canopy, suitable for use as a sun tanning canopy containing a plurality of fluorescent tubes, wherein the said canopy is located on a substantially horizontally extending arm.the free end of which is secured to a sleeve slidably engaging a substantially vertical support column carried on a base for heightwise movement up and down the said column, the weight of the said canopy and sleeve being counterbalanced by means positioned adjacent a side of the said column whereby the vertical position of the canopy may be set at any point between a lowermost position and a position adjacent the top of the support column, the said vertical movement being achieved by light pressure acting on the canopy, said arm or said sleeve.

2. A method according to claim 1 wherein the counterbalancing is achieved by weights positioned within or adjacent the said column carried at one end of a flexible support means the other end of which is attached to the said sleeve, the said flexible support means passing over a pulley means at or adjacent the top of the said column.

3. A method according to claim 2 wherein the said canopy is a sun tanning canopy and includes a plurality of fluorescent tubes and the said counterbalancing weights include the control gear for the said fluorescent tubes.

4. A method according to claim 1 wherein the counterbalancing means comprises a pair of compression/extension coil springs, one spring acting between the said sleeve, or means secured to the said sleeve, and the lower end of the said column and a second spring acting between the sleeve, or means secured to the said sleeve, and means secured at or adjacent the top of the said column.

5. A method according to claim 1 wherein the means for counterbalancing the said canopy comprises a constant force spring having a coiled end and a free end and acting between the said sleeve and a point adjacent the top of the said column.

6. A method according to claim 1, wherein the said column includes a stop means located at a point substantially above the lower end thereof to act to prevent the sleeve, and thereby the canopy, from being moved to a position lower than a predetermined distance above a horizontal surface positioned above the said base.

7. A method according to claim 5 wherein the free end of the constant tension spring is attached at or adjacent the upper end of the column and the coiled end thereof is located at or below the level of the canopy to provide support therefor.

8. A method according to claim 7 wherein the portion of the said spring adjacent the column lies in a vertical channel formed in the said column and the said spring and passes through the front of the said sleeve, the coiled portion bearing against an abutment attached to the said sleeve to provide support for the said canopy.

9. A method according to claim 8 wherein the coiled end of the said spring is retained in the angle formed between a first outwardly and a second downwardly extending arm portion of a support mechanism secured to the said sleeve, the outwardly extending arm portion being urged against an abutment secured to the sleeve or means extending from the sleeve.

10. A method according to the claim 9 wherein the said support for the said spring coil is pivotally mounted at or adjacent the junction of the two arm portions, the downwardly extending portion including a blade element extending towards the said vertical recess in the column and having a portion dimensioned to partially enter the channel formed in the said support column, whereby if the upper end of the spring becomes detached or the spring breaks, the said downwardly extending portion is pivoted toward said channel thereby causing the sides of the said blade to engage the sides of the channel and provide a braking effect and arrest the downward movement of the sleeve and associated canopy.

11. A method according to claim 10 wherein, in the event that the spring breaks or becomes detached from the column the said blade element is urged towards the said channel by a spring means acting between the said sleeve and the said downwardly extending portion.

12. A method according to claim 5 wherein the said support column is rectangular in cross-section and includes vertically extending channels on opposite sides thereof and the said sleeve includes inwardly facing rollers for engagement within the said channels whereby heightwise movement of the sleeve on the column is facilitated.

* * * * *